United States Patent
Nichols et al.

(10) Patent No.: US 6,363,282 B1
(45) Date of Patent: Mar. 26, 2002

(54) APPARATUS AND METHOD TO AUTOMATIC REMOTE SOFTWARE UPDATES OF MEDICAL DEVICE SYSTEMS

(75) Inventors: Timothy Joseph Nichols, Lino Lakes; Kurt R. Linberg, Eden Prairie, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/429,960

(22) Filed: Oct. 29, 1999

(51) Int. Cl.$^7$ .............................................. A61N 1/372
(52) U.S. Cl. ........................................... 607/30; 607/59
(58) Field of Search ..................... 607/30–32, 59–60; 128/903, 904, 920; 600/300

(56) References Cited

U.S. PATENT DOCUMENTS

| | | |
|---|---|---|
| 4,494,950 A | 1/1985 | Fishell |
| 4,886,064 A * | 12/1989 | Strandberg .................. 607/18 |
| 4,987,897 A | 1/1991 | Funke |
| 5,321,618 A | 6/1994 | Gessman |
| 5,345,362 A | 9/1994 | Winkler |
| 5,544,661 A * | 8/1996 | Davis et al. ................. 600/513 |
| 5,752,976 A | 5/1998 | Duffin et al. |
| 5,800,473 A | 9/1998 | Faisandier |
| 5,997,476 A * | 12/1999 | Brown ........................ 600/300 |

FOREIGN PATENT DOCUMENTS

WO          WO 99/14882          3/1999

* cited by examiner

Primary Examiner—George R. Evanisko
(74) Attorney, Agent, or Firm—Girma Wolde-Michael

(57) ABSTRACT

A system and method for providing an automated software update to a programmer or equivalent device used in implantable medical device system is disclosed. The programmer comprises a remote instrument configuration database containing current instrument configuration information. The programmer user interface initiates an interface to a centralized globally accessible remote expert data center located at a distal location relative to the programmer. The remote expert data center includes an instrument configuration database containing configuration data for the programmer. The remote expert data center also includes a released software database containing software applications compatible with the programmer. Further, the remote expert data center contains a rule set database which identifies an approved software application for the programmer. A management component of the remote expert data center enables the transmission of the approved software application to the programmer.

25 Claims, 5 Drawing Sheets

APPARATUS AND METHOD TO AUTOMATIC REMOTE SOFTWARE UPDATES OF MEDICAL DEVICE SYSTEMS

THE FIELD OF THE INVENTION

The present invention relates generally to medical device systems. Specifically, the invention pertains to a remote bi-directional communications with one or more programmable devices that are associated with implantable medical devices. More specifically, the invention relates to an integrated system and method of bi-directional telecommunications between a web-based expert data center and at least one programmer, utilizing various types of network platforms and architecture to implement new software, upgrade software or otherwise perform related diagnoses, on the programmer, to thereby provide an economical and highly interactive system for therapy and clinical care.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinical center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose a serious difficulty and inconvenience for patients who live in rural areas or have limited mobility. Similarly, in the event a need arises to upgrade the software of an implantable medical device, the patient will be required to come into the clinic or hospital to have the upgrade installed.

A further limitation of the prior art relates to the management of multiple implantable devices in a single patient. Advances in modern patient therapy and treatment have made it possible to implant a number of devices in a patient. For example, implantable devices such as a defibrillator or a pacer, a neural implant, a drug pump, a separate physiologic monitor and various other implantable devices may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the performance of the implantable devices on a regular, if not a continuous, basis to ensure optimal patient care. In the absence of other alternatives, this imposes a great burden on the patient if a hospital or clinic is the only center where the necessary frequent follow up, evaluation and adjustment of the medical devices could be made. Moreover, even if feasible the situation would require the establishment of multiple service areas or clinic centers to provide adequate service to the burgeoning number of multi-implant patients worldwide. Accordingly, it is vital to have a programmer unit that would connect to a remote expert medical center to provide access to expert systems and import the expertise to a local environment. This approach would enable unencumbered access to the IMD or the patient.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and/or blood oxygen sensors, are positioned in a patients body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S. Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external programmer for telemetrically programming the modules.

Yet another example of remote monitoring of implanted cardioverter defibrillators is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer is remotely debugged, maintained, upgraded or modified to ultimately enhance the support it provides to the implantable device with which it is associated. Specifically, the Duffin et al disclosure is limited to notifying remote medical support personnel or an operator about impending problems with an IMD and also enables constant monitoring of the patient's position worldwide using the GPS system. However, Duffin et al does not teach the remote programming scheme contemplated by the present invention.

In a related art, Thompson discloses a patient tracking system in a co-pending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which a programmer is remotely evaluated and monitored to effect functional and parametric tune up, upgrade and maintenance as needed.

Yet in another related art, Ferek-Petric discloses a system for communication with a medical device in a co-pending application, Ser. No. 09/348,506 which is incorporated by reference herein in its entirety. The disclosure relates to a system that enables remote communications with a medical device, such as a programmer. Particularly, the system enables remote communications to inform device experts about programmer status and problems. The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek-Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek-Petric's invention advances the art in communications systems relating to interacting with a programmer via a communication medium such as the Internet, the system does neither propose nor suggest remote programming, debugging and maintenance of a programmer without the intervention of a service person.

In yet another related art, Faisandier U.S. Pat. No. 5,800,473 issued on Sep. 1, 1998 provides a system and methods for the automatic update of the software of an external programmer implant that is used to program and configure an active implantable medical device implant and acquire data obtained by the implant. The programmer comprises software composed of an assembly of software objects. The implant comprises a memory containing parametric data for the functioning of the implant and an assembly of software objects necessary for the functioning of the programmer in connection with the parametric data.

One of the limitations of the Faisandier disclosure is the fact that there is no teaching relating to programming the programmer. Specifically, in the context of the present invention, Faisandier does neither teach nor suggest a remote means of programming the programmer. Further, the disclosure fails to disclose the advantageous elements set forth by the present invention. For example, the present invention provides a remotely programmable programmer or control device in communication with a web-based data center worldwide. The programmer is preferably implemented in a multi-implant environment and is capable to manage the operation of the various types of implants.

Accordingly, it would be advantageous to provide a system in which a programmer could uplink to a remote expert data center to import enabling software for self-diagnosis, maintenance and upgrade of the programmer. Yet another desirable advantage would be to provide a system to implement the use of remote expert systems to manage a programmer on a real-time basis. A further desirable advantage would be to provide a communications scheme that is compatible with various communications media, to promote a fast uplink of a programmer to remote expert systems to provide access to specialized data resources. Yet another desirable advantage would be to provide a high speed communications scheme to enable the transmission of high fidelity data to install software in the programmer. Another desirable advantage would be to provide a software management system based on manufacturer's approved or Government approved status to enable a quick upgrade of compliant software in medical devices. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer, located in close proximity to the IMDs. Some of the most significant advantages of the invention include the use of various communications media between the remote web-based expert data center and the programmer to remotely debug, update or install new software to ultimately effect real-time parametric and operational changes, as needed.

In the context of the present invention, one of the many aspects of the invention includes a real-time access of a programmer to a remote web-based expert data center, via a global communication network, which includes the Internet. The operative structure of the invention includes the remote web-based expert data center, in which an expert system is maintained, having a bidirectional real-time data, sound and video communications with the programmer via a broad range of global communication link systems. The programmer is in turn in telemetric communications with the IMDs such that the IMDs may uplink to the programmer or the programmer may down link to the IMDs, as needed.

In yet another context of the invention, the critical components and embedded systems of the programmer are remotely maintained, debugged and/or evaluated to ensure proper functionality and performance by down linking expert systems and compatible software from the web-based expert data center.

In a further context of the invention, a programmer is remotely monitored, assessed and upgraded as needed by importing expert software systems from a remote expert data center via a wireless or equivalent communications system. The operational and functional software of the embedded systems in the programmer may be remotely adjusted, upgraded or changed as apparent. Some of the software changes may ultimately be implemented in the IMDs as needed by down linking from the programmer to the IMDs.

Yet another context of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communications system. However, it should be noted that the communication systems, in the context of this invention, are interchangeable and may relate to various schemes of cable, fiber optics, microwave, radio, laser and similar communications or any practical combinations thereof.

Some of the distinguishing features of the present invention include the use of a robust web-based expert data center, accessible worldwide, to manage and tune software relating to the operational and functional parameters of a programmer in real-time. Specifically, the invention enables remote diagnosis, maintenance, upgrade, performance tracking, tuning and adjustment of a programmer from a remote location.

Although the present invention focuses on remote real-time software systems monitoring and management of the programmer, some of the changes and upgrades made to the programmer could advantageously be transferred to the IMDs. This is partly because some of the performance parameters of the programmer are functionally parallel to those in the IMDs. Thus, one additional benefit of the present invention is an enhancement of the programmer may be implemented, on a proactive basis, in the IMDs by down linking from the programmer thereby upgrading the IMDs to promote the patient's well being.

Yet one of the other distinguishing features of the invention includes the use a highly flexible and adaptable communications scheme to promote continuous and real-time data communications between a remote expert data center and a programmer associated with a plurality of IMDs. The IMDs are structured to share information intracorporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant advantages over the prior art by enabling remote software troubleshooting, maintenance and upgrade to the programmer. The communications scheme enables remote debugging and analysis on the programmer. In the event a component or software defect is noted, the system is able to check whether a 'remote-fix' is possible. If not, the system broadcasts an alert to an operator thus attending to the problem on a real-time basis. In the execution of this function the communications scheme of the present invention performs, inter alia, a data base integrity and the mean time between failures status of all the significant and relevant components and the associated embedded systems. Further, patient history, performance parameter integrity and software status are mined from the programmer's database and analyzed by an analyzer at the remote expert data center.

The invention provides significant compatibility and scalability to other web-based applications such as telemedicine and emerging web-based technologies such as tele-immersion. For example, the system may be adapted to webtop applications in which a webtop unit may be used to uplink the patient to a remote data center for non-critical information exchange between the IMDs and the remote expert data center. In these and other web-based similar applications the data collected, in the manner and substance of the present invention, may be used as a preliminary screening to identify the need for further intervention using the advanced web technologies.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DESCRIPTION OF THE PREFERRED EMBODIMENTS

Figure 1:
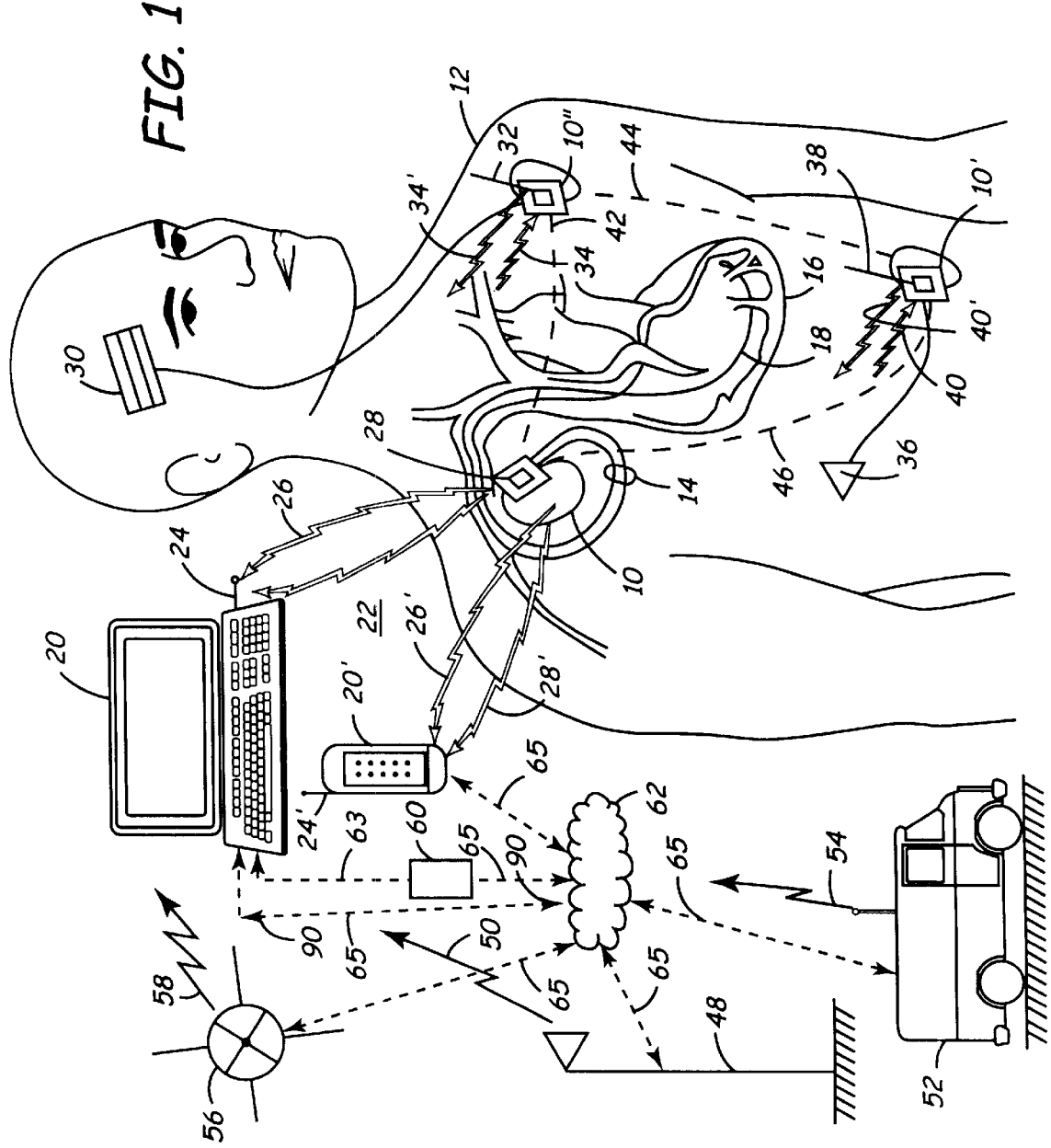
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bidirectional wireless communications system between programmer 20, webtop unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and webtop unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or webtop unit 20' and data center 62. The communications link between Programmer 20 or webtop unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, webtop unit 20', mobile vehicle 52 and satellite 56 are in communications with data center 62 via wireless link 65. Further, mobile system 52 and satellite 56 are in wireless communications with programmer 20 or webtop unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

Figure 2:
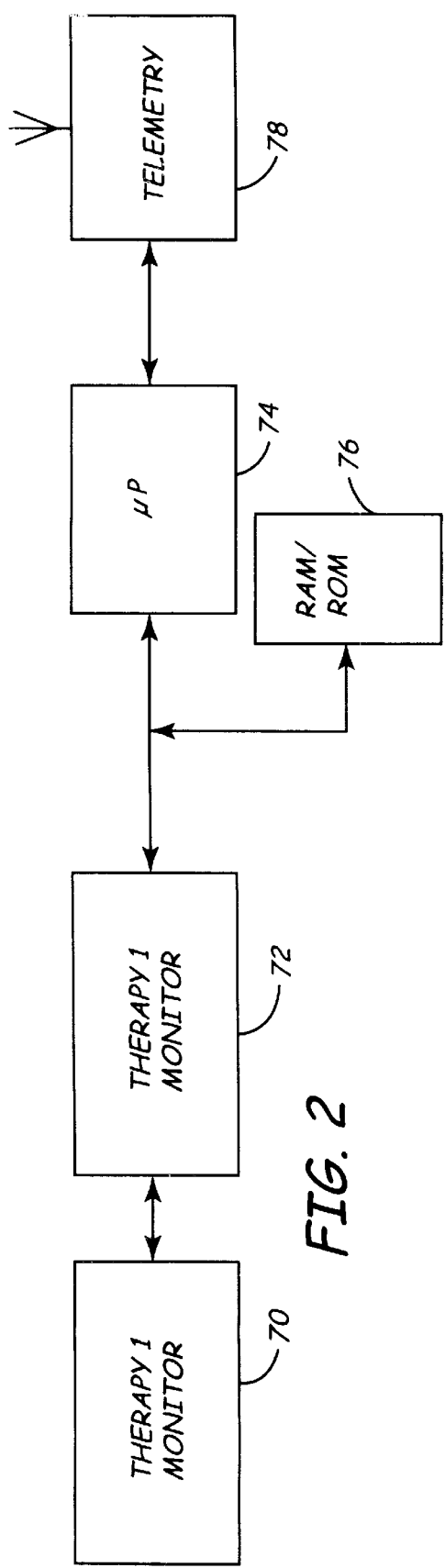
FIG. 2 is a block diagram representing the major components of an IMD.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patients skin overlying IMD 10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

Figure 3B:
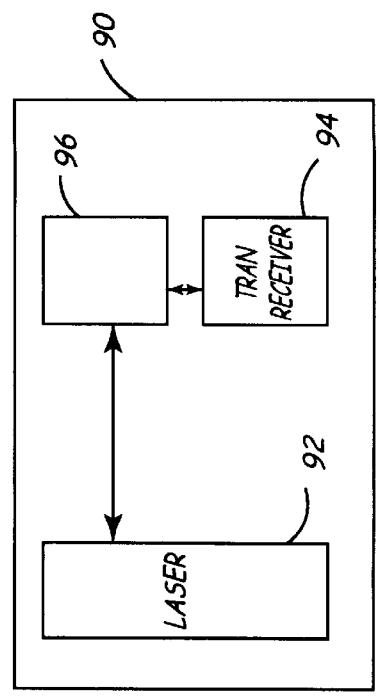
FIG. 3B is a block diagram representing a laser transceiver for high speed transmission of voice, video and other data.
Figure 3A:
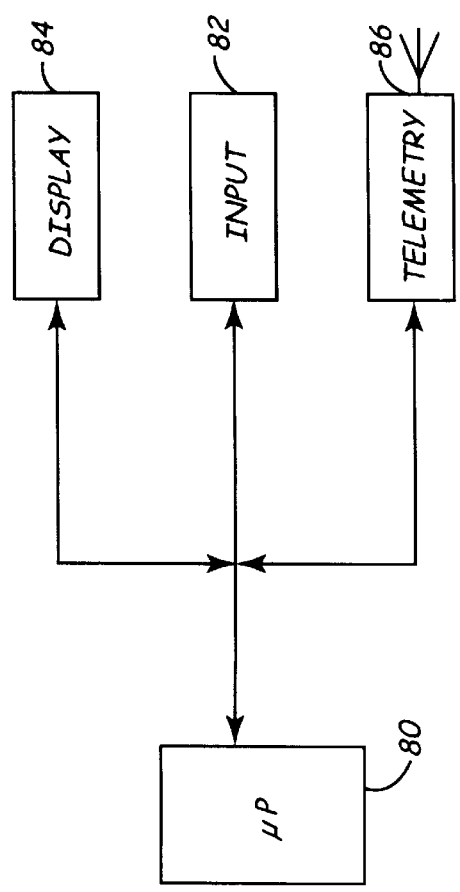
FIG. 3A is a block diagram presenting the major components of a programmer or webtop unit.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or webtop unit 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
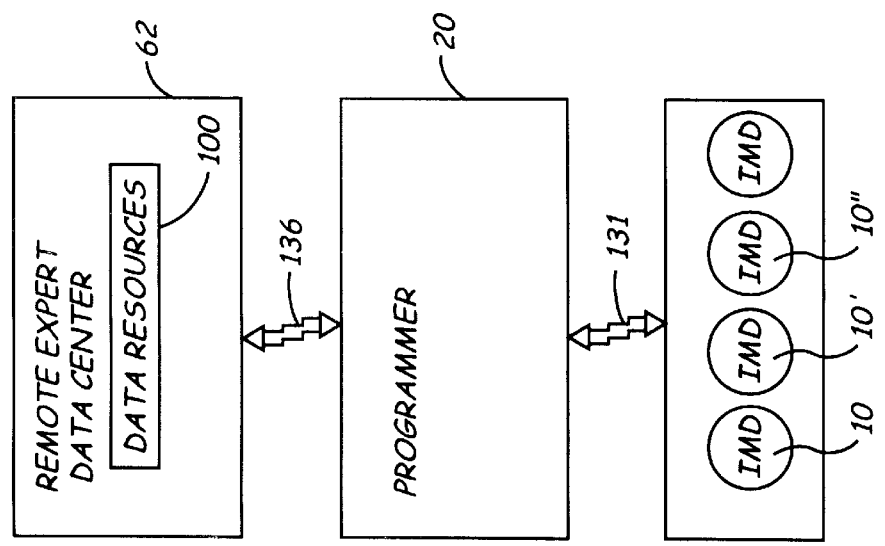
FIG. 4 is a block diagram illustrating the organizational structure of the wireless communication system in accordance with the present invention.

FIG. 4 is a simplified block diagram illustrating the principal systems of the invention. The Remote expert system or data center 62 includes data resource 100. As discussed hereinabove, data center 62 is preferably in wireless communications with programmer 20. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDS, distributed throughout the world, may be implemented and the practice of the present invention does not limit the number of implants per se.

Figure 5:
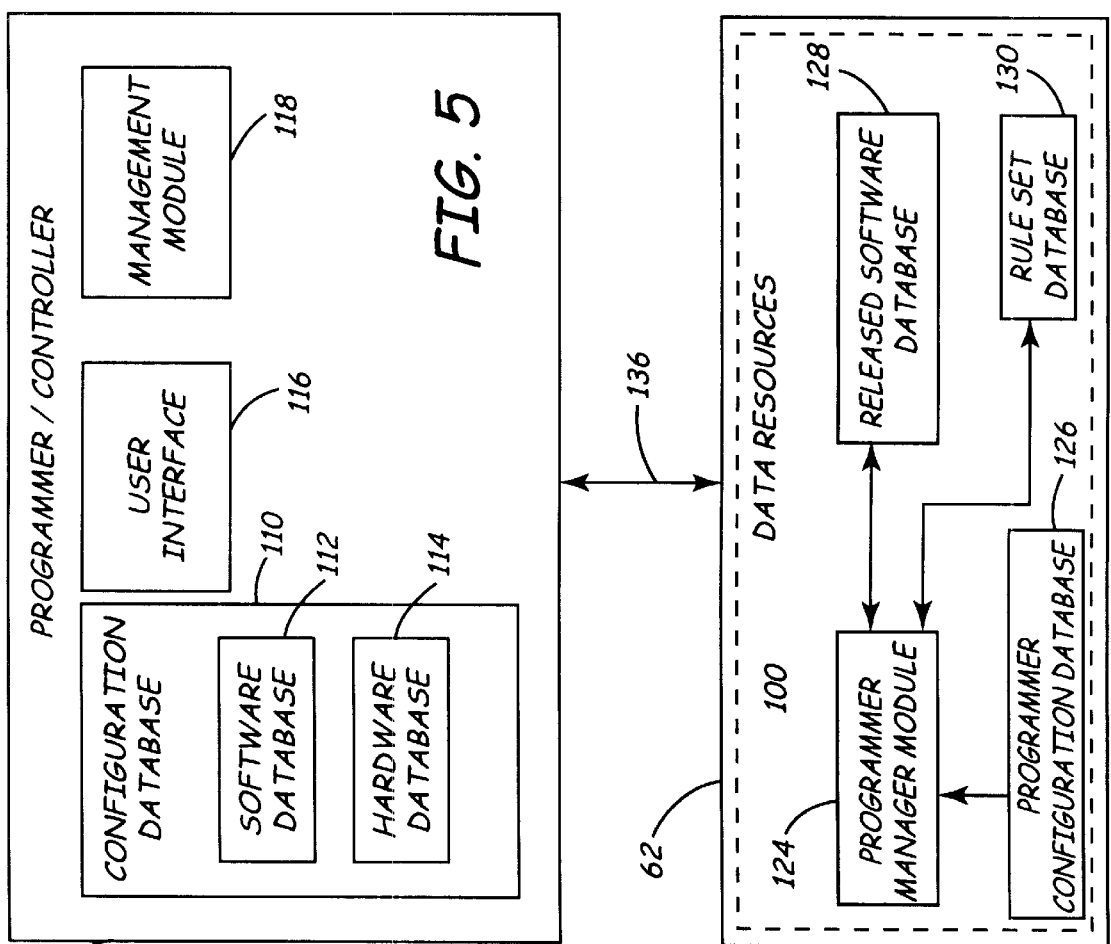
FIG. 5 is a block diagram illustrating further component details of the structure depicted in FIG. 4.

FIG. 5 is a representation of the major functional components of Programmer 20, data resources 100 and the wireless data communication 136. Specifically, as discussed hereinabove, programmer 20 includes configuration database 110. Configuration data base further includes software data base 112 and hardware database 114. Similarly, user interface 116 and management module 118 are contained in programmer 20. These systems form the high level software upgradeable systems with which remote data center 62 must interact to upgrade the software in programmer 20.

Programmer 20 is connected to remote expert data center 62 via bi-directional data communication link 136. Remote expert data center 62 forms the web-based data resources/ expert system 100. Accordingly, data resources system 100 is a sub-component of remote data center 62. Data resources 100 contains, inter alia, Programmer manager module 124 which is in bi-directional operable data communications with programmer configuration data base 126, released software database 128 and rule set database 130. The databases and the module form the significant elements in which upgradable software including Government approved software reside. The data and related software are transmitted to programmer 20 via one or a combination of the communications channels outlined hereinabove.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus, also coupled to a graphics circuit, which is used to point to various locations on screen/display to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. The graphics display/screen 84 is also used to display patient related data and menu choices and data entry fields used in entering the data in accordance with the present invention as described below. Graphics display/screen 84 also displays a variety of screens of telemetered out data or real time data. Programmer 20 is also provided with a strip chart printer or the like coupled to interface controller module so that a hard copy of a patient's ECG, EGM, marker channel or similar graphics display can be generated. Further, Programmer 20's history relating to instrumentation and software status may be printed from the printer. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor (Reveal), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

Data resources 100 represents a high speed computer network system which is located in remote expert data center 62 having wireless bi-directional data, voice and video communications with programmer 20 via wireless communications link 136. Generally data resources 100 are preferably located in a central location and are equipped with high-speed web-based computer networks. Preferably, the data resource center is manned 24-hours by operators and clinical personnel who are trained to provide a web-based remote service to programmer 20. Additionally, as discussed hereinabove, data resources 100 provide remote monitoring, maintenance and upgrade of programmer 20. The location of remote data center 62 and, consequently, the location of data resources 100 are dependent upon the sphere of service. In accordance with the present invention, data resource 100 may be located in a corporate headquarters or manufacturing plant of the company that manufactures programmer 20. Wireless data communications link/connection 136 can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bi-directional wireless communications 136 acts as a direct conduit for information exchange between remote data center 62 and programmer 20. Further, bidirectional wireless communications 136 provides an indirect link between remote data center and IMDs 10, 10' and 10" via programmer 20. In the context of this disclosure the word "data" when used in conjunction with bi-directional wireless communications also refers to sound, video and information transfer between the various centers.

Referring to FIG. 5, programmer configuration database 110 includes information and data specifying both the hardware configuration and the software applications or programs installed on various programmers, including programmer 20. For example, configuration database 110 may include information as to the amount of random access memory (RAM) of programmer 20. Depending upon the amount of RAM within programmer 20, a software application may need to be adjusted accordingly prior to installation to ensure compatibility between programmer 20 and the software application to be installed. Programmer manager module 124 provides any adjustments to the software application prior to installation.

Release software database 128 is a software database which includes all current software applications or programs developed and configured for various programmers, including programmer 20 connected to data center 62 via data communications link/connection 136.

Rule set database 130 is a database which includes information and data related to specific rules and regulations regarding various software applications for programmer 20. For example, rule set database 130 includes information relating to whether a particular software application can be released and installed in a particular country or whether the software may not be installed due to lack of approval by a governing body, such as an agency or regulatory branch within the particular country. Rule set database 130 also includes information regarding whether the manufacturer, owner, or licensee of the software application has approved installation of the software application into programmer 62. In some instances, a software manufacturer, owner, or licensee may want or need to prevent installation of a software program at the present time due to company policy or strategy.

An operator located at a site remote from information network 62 may interconnect one or more programmers of programmer 20 to information network 62 via data communications link/connection 136 for a variety of reasons. For example, an operator may retrieve information from an implantable medical device, such as IMD 10, and transfer this information to data center 62 for storage or evaluation. Similarly, an operator may interface programmer 20 with information network 62 to review a variety of information regarding a particular programmer, such as IMD 10, stored on information network 62. For example, an operator may interface with a help module located on information network 62.

Regardless of the purpose for which programmer 20 is connected and interfaced with information network 62 (via data communications link/connection 136), information network 62 will automatically review the hardware configuration and software applications of various microprocessor-based instruments of programmer 20. Based upon user performance, an updated software application will be installed automatically, if available and approved for installation in a particular programmer. In some cases, the software installation is a byte level update to software already residing in the instrument. In other cases, the software installation is a new application replacing an out dated application. In one embodiment, the operator can acquiesce to the software installation. The operator can also deny or defer installation of the software via touch-sensitive display screen 84 of programmer 20 as previously discussed herein. For example, an operator may deny or defer a software application installation if programmer 20 is presently engaged in a medical procedure with an IMD. This safety feature eliminates interference with programmer-IMD sessions/procedures.

Figure 6:
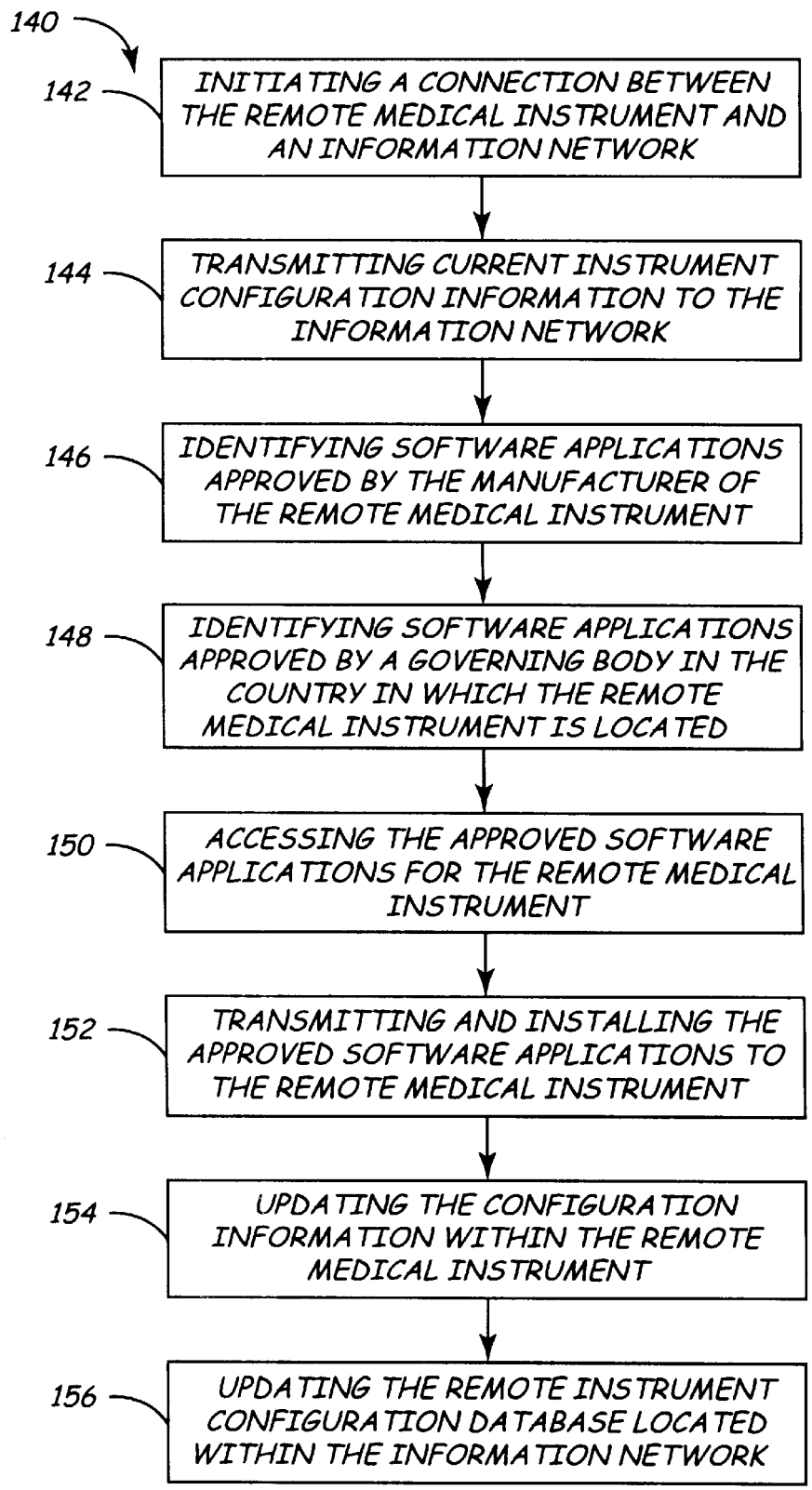
FIG. 6 represents flow charts relating to a high level operational logic of the invention as it relates to functional elements of the components.

FIG. 6 is flow chart describing method 140 of automatically providing updated software to programmer 20. The system logic for the method is initiated at step 142, data communication media/connection 120 is initiated between programmer 20 and information network 122. Data communications link/connection 120 can be a LAN connection, an internet connection, a telephone line connection, a satellite connection, a constellation of satellites, a GPS connection, any combination thereof, or an equivalent communications link. Data communications link/connection 120 is preferably initiated by remote instrument user interface 116 of programmer 20. However, data communications link/connection 120 could also be initiated by information network 122 via programmer manager module 118. Also, the interface between programmer 20 and information network 122 can be a direct or an indirect interface through other programmers. For example, IMD 10 can be connected to information network 122, programmer 20, and data communications link/connection 120. At step 144, current instrument configuration information is transmitted from programmer 20 to information network 122. This information includes both the current hardware configuration and software applications of programmer 20.

At step 146, software applications which are approved by a manufacturer, owner, or licensee of programmer 20 are identified. At step 148, software applications which are approved by a governing body or agency in the country in which programmer 20 is located are identified. At step 150, software applications which has been approved by both the manufacturer or owner and the governing body or agency in the country in which programmer are accessed. The approved software applications are transmitted to and installed in programmer 20 via data communications link/connection 120, as shown at step 152. Programmer configuration data base 110 is updated using the necessary and proper software as shown under logic step 154. Similarly, programmer database located in information network 130 is updated regarding the software installation, as shown at step 156.

Figure 7:
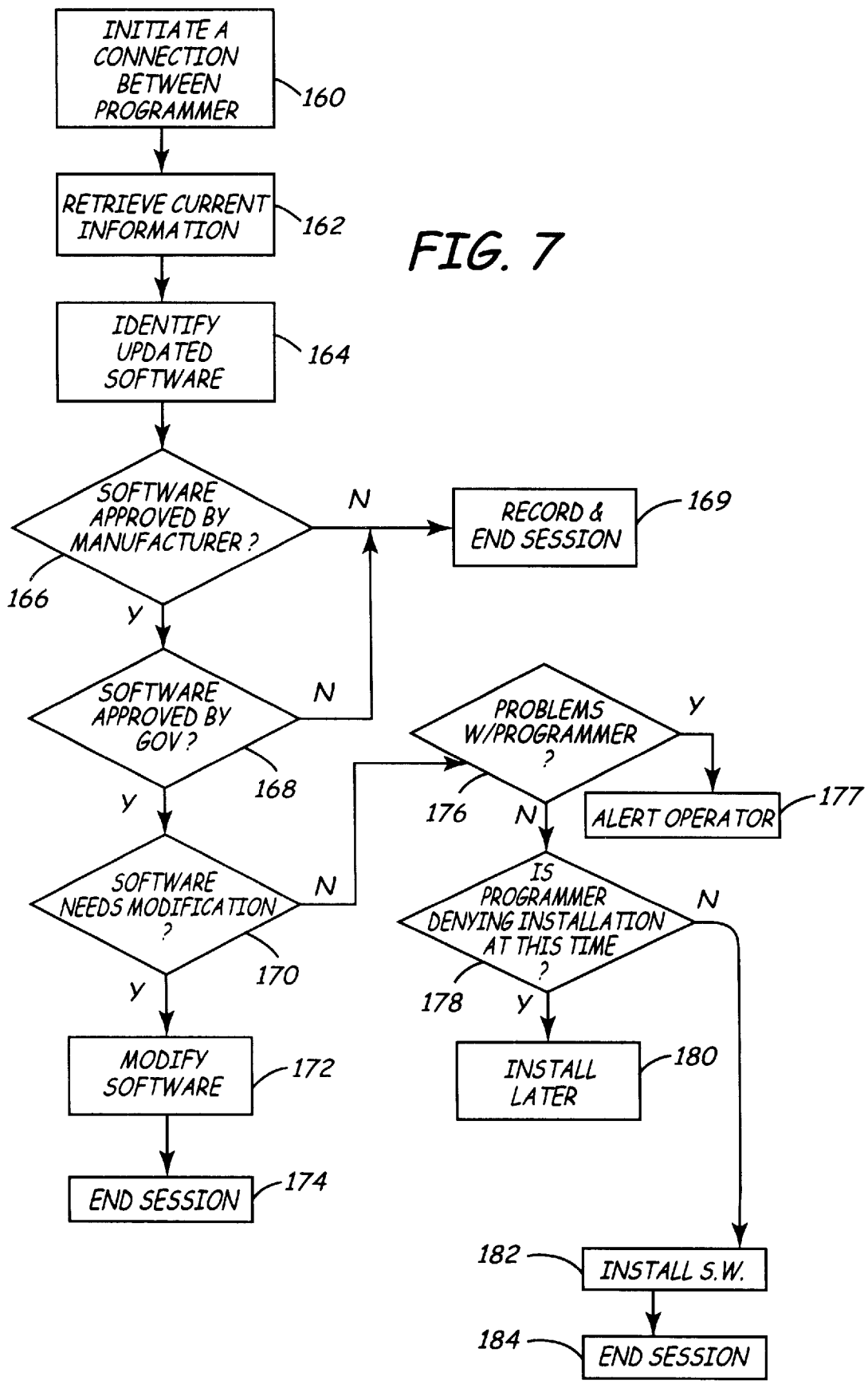
FIG. 7 represents flow charts relating to component hardware and database management logic for implementing remote software upgrade as needed.

FIG. 7 is a flow chart illustrating the various decisions necessary to install updated software applications on programmer 20. At step 160, data communications link/connection 136 is initiated between programmer 20 and data center 62. As previously discussed, this connection can be a LAN connection, an internet connection, a telephone line connection, a satellite connection, a constellation of satellites, a GPS connection, any combination thereof, or any equivalent communications system. Further, the connection can be a direct connection or an indirect connect via other programmers. At step 162, current hardware configuration and software applications are retrieved from programmer configuration database 110. Programmer manager module 124 of data center 62 retrieves the remote instrument configuration via data communications link/connection 136 and programmer management module 118 of programmer 20.

At step 164, programmer management module 118 identifies updated software applications via released software database 128. At decision step 166, a determination is made if an updated software application is approved for installation by a manufacturer, owner, or licensee of the software. If the software application is not approved for installation to programmer 20, the software application is not provided and the logic proceeds to step 169 where the event is recorded and the session terminated. If the updated software application is approved by the manufacturer, owner, or licensee of the software, it is then determined whether the software application is approved by a governing body, such as a government agency of a country in which programmer 20 is located. This decision is shown at decision step 168. If the updated software application is not approved by the governing body, the software application update is not installed and the logic advances to step 169 where the event is recorded and the session terminated.

If the software application has been approved by the governing body, a determination is made as to whether the updated software needs to be modified prior to installation into programmer 20, as shown at decision step 170. If the updated software needs to be modified, this modification is made based upon the programmer configuration in programmer configuration data base 110 and programmer configuration database 126, as shown at step 172. If the software in programmer 20 needs modification, the logic will advance to decision step 176 where the existence of problems with programmer 20 is checked. If there are problems with the programmer 20, the logic proceeds to step 177 where an alert is flagged or broadcast to the operator. In the event there are no problems, with programmer 20, the logic proceeds to decision step 178 where it is checked if programmer 20 is denying or deferring installation. If not, the logic proceeds to install the software under logic step 182 and the session is terminated at step 184. In the alternate, if it is confirmed that programmer 20 is denying installation of the software, installation is scheduled for a later time under step 180.

Once the software application is in the proper format to be installed into programmer 20, a determination is made as to whether the operator of programmer 20 is denying or deferring installation of the software application at the present time, as shown at decision step 178. Software installation may be denied or deferred if programmer 20 is in the process of performing one of a variety of tasks, such as retrieving information from IMD 10. If the operator of programmer 20 is denying a software installation, no software application is provided, as discussed hereinabove. Similarly, if the operator of programmer 20 is deferring installation at any time, the software application will be installed at a later time, as shown at step 180. Finally, if the operator of programmer 20 is acquiescing to the installation of the updated software application at this time, the updated software application is installed onto programmer 20, as shown at step 180.

Accordingly, the present invention advantageously provides a method and process by which a remote programmer or any control device capable of monitoring the operations of an IMD or a plurality of IMDs can be debugged, monitored and programmed using a web-based globally distributed smart system. Specifically, some of the advantages of the invention include automated software update transmitted from an expert data center to a globally distributed sets or groups of programmers, each serving one or more IMDs. One of the many advantages of the software distribution and management system of the present invention includes the system's capability to adapt to a web-based telemetric/wireless communication system. Specifically, the use of a globally accessible expert data center for serving a highly distributed network of programmers significantly advances patient service. Further, the Internet compatible, preferably web-based expert data center is implemented to upgrade, update, correct and modify the operational and functional software of the programmer, which in turn may upgrade the IMDs by downlinking to the IMDs to transfer the software application as needed.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. In a bi-directional communications system wherein a web-based remote expert data center is in remote communications with a programmer for an implantable medical device, a method for providing an automated software update to the programmer from the expert data center, the method comprising the steps of:

initiating an interface between the programmer and a remote expert data center;

retrieving current instrument configuration information from an instrument configuration database located within the programmer;

determining an approved software application for the programmer;

accessing the approved software application;

transmitting the approved software application to the programmer via the interface; and updating a remote instrument configuration database located within the remote expert data center.

2. The method of claim 1, and including the further step of:

updating an instrument configuration data base located within the programmer.

3. The method of claim 1, wherein the step of initiating an interface includes the further step of:

initiating an interface via a local area network communications link between the programmer and the remote expert data center.

4. The method of claim 1, wherein the step of initiating an interface includes the further step of:

initiating an interface via an internet communications link between the programmer and the remote expert data center.

5. The method of claim 1, wherein the step of initiating an interface includes the further step of:

initiating an interface via a telephone line communications link between the programmer and the remote expert data center.

6. The method of claim 1, where the step of initiating an interface includes the further step of:

initiating an interface via a satellite communications link between the programmer and the remote expert data center.

7. The method of claim 1, where the step of initiating an interface includes the further step of:

initiating an interface via a global positioning system communications link between the programmer and the remote expert data center.

8. The method of claim 1, wherein the step of initiating an interface includes the further step of:

initiating an interface between the programmer and the remote expert data center via at least two communication links selected from the group of communication links consisting of a local area network link, an internet link, a telephone line link, a satellite link, a global positioning system link, and a combination thereof.

9. The method of claim 1, wherein the step of determining an approved software application includes the further step of:

determining an approved software application for the programmer based upon approval of the application by a government agency in a country in which the programmer is located.

10. The method of claim 1, wherein the step of determining an approved software application includes the further step of:

determining an approved software application for the programmer based upon manufacture approval of the application.

11. The method of claim 1, and including the further step of:

modifying the approved software application based upon the instrument configuration information of the programmer prior to transmitting the approved software application to the programmer.

12. A method for providing an automated software update to a programmer of an implantable medical device system, the method comprising the steps of:

initiating an interface between a programmer and a remote expert data center located at a distant location relative to the programmer;

retrieving current instrument configuration information from an instrument configuration database located within the programmer;

identifying an approved software application for the programmer; and transmitting the approved software application to the programmer via the interface.

13. The method of claim 12, and including the further step of:

updating an instrument configuration database located within the programmer.

14. The method of claim 12, and including the further step of:

updating a remote instrument configuration database located with the remote expert data center.

15. The method of claim 12, wherein the step of initiating an interface includes the further step of:

initiating an interface between the programmer and the remote expert data center via a local area network communications link.

16. The method of claim 12, wherein the step of initiating an interface includes the further step of:

initiating an interface between the programmer and the remote expert data center via an internet communications link.

17. The method of claim 12, wherein the step of initiating an interface includes the further step of:

initiating an interface between the programmer and the remote expert data center via a telephone line communications link.

18. The method of claim 12, where the step of initiating an interface includes the further step of:

initiating an interface between the programmer and the remote expert data center via a satellite communications link.

19. The method of claim 12, where the step of initiating an interface includes the further step of:

initiating an interface between the programmer and the remote expert data center via a global positioning system communications link.

20. The method of claim 12, wherein the step of initiating an interface includes the further step of:

initiating an interface between the programmer and the remote expert data center via at least two communication links selected from the group of communication links consisting of a local area network link, an internet link, a telephone line link, a satellite link, a global positioning system link, and a combination thereof.

21. The method of claim 12, wherein the step of identifying an approved software application includes the further step of:

identifying an approved software application for the programmer based upon approval of the application by a government agency in a country in which the programmer is located.

22. The method of claim 12, wherein the step of identifying an approved software application includes the further step of:
   identifying an approved software application for the programmer based upon manufacturer approval of the application.

23. The method of claim 12, and including the further step of:
   modifying the approved software application based upon the instrument configuration information of the programmer prior to transmitting the approved software application to the programmer.

24. A system for providing an automated software update to a programmer of an implantable medical device system, the system comprising:
   means for initiating an interface between a programmer and a remote expert data center located at a distant location relative to the programmer;
   means for retrieving current instrument configuration information from an instrument configuration database located within the programmer;
   means for determining an approved software application for the programmer;
   means for accessing the approved software application;
   means for transmitting the approved software to the programmer;
   means for updating a remote instrument configuration database located within the remote expert data center; and
   means for updating the instrument configuration database located within the programmer.

25. A system for providing an automated software update to a programmer of an implantable medical device system, the system comprising:
   means for initiating an interface between a programmer and a remote expert data center located at a distant location relative to the programmer;
   means for retrieving current instrument configuration information from an instrument configuration database located within the programmer;
   means for identifying an approved software application for the programmer; and
   means for transmitting the approved software application to the programmer.

* * * * *